United States Patent [19]

Ulrich et al.

[11] Patent Number: 5,108,930
[45] Date of Patent: Apr. 28, 1992

[54] AMINOGUANIDINE ASSAY AND APPLICATIONS THEREOF

[75] Inventors: Peter C. Ulrich, Tenafly, N.J.; Zee M. Look, Wesley Hills, N.Y.

[73] Assignee: Alteon Inc., Northvale, N.J.

[21] Appl. No.: 469,964

[22] Filed: Feb. 20, 1990

[51] Int. Cl.⁵ .............................................. G01N 33/00
[52] U.S. Cl. ..................................... 436/111; 436/808; 436/63; 436/161; 422/61; 422/70; 435/810
[58] Field of Search ................. 436/111, 808, 63, 161; 422/61, 70; 435/810

[56] References Cited

U.S. PATENT DOCUMENTS 4,758,583 7/1988 Cerami et al. ....................... 435/260

OTHER PUBLICATIONS

Beaven et al. "A Specific And Sensitive Assay For Aminoguanidine: Its's Application To A Study Of The Disposition Of Aminoguanidine In Animal Tissue", J. Pharmacol. Exp. Ther., vol. 165, No. 1, 1969, pp. 14–22.

Primary Examiner—Robert J. Warden
Assistant Examiner—Lyle A. Alexander
Attorney, Agent, or Firm—Klauber & Jackson

[57] ABSTRACT

A method and associated materials including test kits for detecting and measuring the presence and amount of aminoguanidine and its analogs in biological samples is disclosed. Biological samples may include plasma, urine or tissue, and the present method may be used to determine the activity and effect of aminoguanidine and its analogs, particularly to the extent that such materials are useful as agents to prevent advanced glycosylation of proteins. The present invention extends to a new drug assay, suitable test kits, and to the assessment of kidney function and the potential to aid in the diagnosis of underlying pathologies where kidney dysfunction is a symptom.

17 Claims, 7 Drawing Sheets

FIG.1

TYPICAL CHROMATOGRAMS
(A): BLANK HUMAN PLASMA
(B): LOW CONCENTRATION (0.1 mcg/mL) QC SAMPLE
(C): HIGH CONCENTRATION (8 mcg/mL) QC SAMPLE

TYPICAL CHROMATOGRAMS
(A): BLANK HUMAN URINE
(B): LOW CONCENTRATION (1.0 mcg/mL) QC SAMPLE
(C): HIGH CONCENTRATION (90 mcg/mL) QC SAMPLE

AMINOGUANIDINE ASSAY AND APPLICATIONS THEREOF

The present invention relates to an assay for aminoguanidine and its analogs, and particularly to the measurement of aminoguanidine and its analogs in body fluids.

The compound aminoguanidine has been studied extensively over the years and, in particular, was originally identified as having certain physiological properties, among them an inhibitory action on the enzyme histaminase. Aminoguanidine has been identified as a selective inhibitor of diamine oxidase and has accordingly been administered both to animals and humans to study histamine metabolism. In particular, aminoguanidine is known to increase levels of histamine, as noted in Lindbergh et al., "The Inhibitory Effect of Aminoguanidine on Histamine Catabolism in Human Pregnancy," ACTA OBSTET. GYNECOL. SCAND., 45:131-139, 1966. More recently, aminoguanidine has been identified as an inhibitor of glucose-mediated cross-linking of proteins and as such, possesses utility in the treatment of conditions resulting from nonenzymatic protein crosslinking, such as the long-term complications of diabetes mellitus. This recently discovered role of aminoguanidine is set forth in U.S. Pat. No. 4,758,583, by Cerami, Ulrich and Brownlee, issued Jul. 19, 1988, and accordingly, the relevant portions thereof are incorporated herein by reference.

As a result of the earlier discovered use of aminoguanidine to study histamine metabolism, efforts have been made to develop appropriate assays to examine the disposition of aminoguanidine in living tissues. In particular, Beaven et al., J. PHARMACOL. EXP. THER., 165:14-22, 1969, developed a colorimetric assay for aminoguanidine based upon its reaction with p-nitrobenzaldehyde in an acid solution. The reaction product yielded a material having an intense yellow color which could then be isolated from endogenous substances by extraction into ethyl acetate and back into dilute hydrochloric acid. The hydrochloric acid extract would then be made alkaline, and the yellow product could be assayed spectrophotometrically.

While the procedures identified in Beaven et al. offer a suitable assay for individualized investigation, the impending emergence of aminoguanidine as a therapeutic agent has motivated the development of a more sophisticated assay that may be capable of operation on an automated basis for the rapid batch-wise analysis of biological specimens for the compound. Such an assay would facilitate the efficient, rapid and accurate management of aminoguanidine therapy as contemplated under U.S. Pat. No. 4,758,583, as well as assisting in the identification of potential new activities and utilities for this compound.

In addition, it is desirable to develop such an assay that will be useful not only with aminoguanidine but with analogs thereof which are likewise under development for use and application in accordance with the teachings outlined in the aforementioned U.S. patent, and metabolites of AG (aminoguanidine) or its analogs, whose presence would be important to measure.

SUMMARY OF THE INVENTION

In accordance with the present invention, an assay method and associated materials have been developed that offers an expeditious and accurate means for identifying the presence and disposition of aminoguanidine and its analogs in biological samples such as plasma and body tissues. In its essential aspects, therefore, the present invention comprises a method for assaying aminoguanidine and its analogs by:

A. gathering a biological sample believed to contain a quantity of aminoguanidine or analogs thereof;

B. deproteinizing the biological sample;

C. reacting the deproteinized biological sample of Step B with a pyridine aldehyde in an amount sufficient to convert any aminoguanidine or analogs thereof present in said biological sample to the corresponding pyridinealdehyde-substituted hydrazone;

D. isolating any substituted hydrazone formed in Step C from the remainder of the reaction mixture by high pressure liquid chromatography employing a gradient elution; and E. examining the isolate of Step D to assess the quantity and disposition of said aminoguanidine and/or its analogs.

The biological sample may be deproteinized by treating it with an effective amount of a deproteinizing agent or selected from a moderate to strong acid suitable for precipitating protein, and a suitable organic solvent; or by subjecting the sample to ultra filtration to remove the protein. Suitable acids include perchloric acid and trichloroacetic acid, while suitable solvents include methanol, acetonitrile and methylene chloride. The pyridine aldehyde may preferably comprise 6-methyl-2-picolinaldehyde which would correspondingly form 6-methyl-2-picolinaldehyde guanylhydrazone, in the instance where aminoguanidine is the compound being assayed. Preferably, the reaction between the biological sample and pyridine aldehyde is conducted under mildly acidic conditions, and the chromatographic protocol utilizes a radial compression chromatographic column and proceeds with an isocratic flow rate and under paired-ion conditions. In the absence of radial compression technology, similar packing materials in a steel column may be substituted, although chromatographic adjustments may be necessary. Lastly, the hydrazone isolate may be examined by ultraviolet spectroscopy and, in the instance of aminoguanidine, is detectable at a wavelength of about 302 nm.

The above procedure possesses numerous applications and, in particular, will facilitate the measurement of aminoguanidine in the instance where it is being administered to combat the deleterious effects of diabetes and aging, to determine whether aminoguanidine was, in fact, administered and, if so, whether adequate body fluid levels of aminoguanidine have been achieved to have the desired effect and, as an adjunct to the last-mentioned, will further facilitate the adjustment of the administrative protocol to achieve effective levels of aminoguanidine in body fluids. Thus, for example, the present assay method may be utilized with biological fluids such as urine, saliva, tissue homogenates, and plasma.

As indicated earlier herein, the method of detecting and measuring aminoguanidine by means of the present assay is applicable to analogs of aminoguanidine. As an exemplary analog, N-ethyl aminoguanidine is disclosed later on herein and has been utilized as an internal standard in the present assay system and illustrates the applicability of the assay system to other analogs of aminoguanidine. Aminoguanidine might be used as the internal standard for an analog, as long as aminoguanidine was not a suspected or known metabolite of the analog and its concentration in need of measurement.

Corresponding utility of the present assay extends to the instance where the biological sample is tissue. Accordingly, the present invention extends to a method of measuring the presence of aminoguanidine and/or its analogs in tissue by gathering one or more tissue samples and performing the assay of the invention with the samples. Thus, tissues such as kidney, collagen, blood vessels and the like may be similarly examined for both experimental animal studies and human biopsy studies, to measure aminoguanidine or analog levels in such tissues, for the purpose of determining whether such levels are adequate and, in the case of newly discovered aminoguanidine derivatives, to determine whether such derivatives are capable of becoming localized in the desired tissues in order to exert the desired therapeutic inhibitory effect.

The present invention further extends to a method for measuring kidney function by the measurement of the elimination half-life of aminoguanidine or an analog thereof, and in a particular embodiment, may be practiced by resort to the present assay. Accordingly, the measurement of kidney function may proceed by the gathering of a plasma sample from the host subject, treating the plasma sample with a chlorinated organic acid in an amount sufficient to deproteinize the plasma sample; reacting the deproteinized plasma sample with a pyridine aldehyde preferably under mildly acidic conditions to form a pyridine aldehyde substituted hydrazone; isolating any hydrazone formed by high pressure liquid chromatography and examining the isolate for aminoguanidine or analogs, preferably by ultraviolet spectroscopy.

The entire assay and protocol includes the administration of a fixed dose of aminoguanidine or an analog, followed by the collection of plasma samples at various time intervals, performance of the present method to thereby determine aminoguanidine content in each sample and by calculation, aminoguanidine elimination data, and comparison of this data against that obtained from the graphical or tabular continuum of previously collected data of elimination of aminoguanidine gathered from subjects with a range of kidney function, in order to determine the kidney function of the subject presently being examined.

The present invention also covers a test kit for the performance of the present assay. The test kit comprises:

A. a quantity of an agent for use in deproteinization of the biological sample;

B. a quantity of a pyridine aldehyde for reaction with available aminoguanidine or analog compounds;

C. other reagents and substrates used in high pressure liquid chromatography; and D. directions for use of the kit.

Suitable deproteinizing agents may be selected from the group consisting of moderate to strong acids suitable for precipitating protein, and suitable organic solvents. Both the acids and the solvents are listed earlier herein. The present test kit may also include an internal standard selected from aminoguanidine and its analogs, such as for example, the aminoguanidine analog N-ethyl aminoguanidine.

In the instance where the test kit is prepared for use in the measurement of kidney function, it may include a quantity of aminoguanidine or an analog thereof in a premeasured dosage form suitable for administration to a test subject, and a graphical or tabular continuum of quotients or a formula derived from such a continuum determined from the reconciliation of the elimination half-life ($T_{\frac{1}{2}}$) of aminoguanidine or its analogs with the Glomerular Filtration Rate (GFR), to which the diagnostician and clinician may refer to interpret the results of the test in terms of kidney operability.

The predetermined dosage form may be prepared for oral administration and may comprise either a solid or liquid form, with tablets, capsules, elixirs and syrups contemplated. The quotients comprise indices derived from the ratios of the elimination half-life ($T_{\frac{1}{2}}$) of aminoguanidine or its analogs with the Glomerular Filtration Rate (GFR).

The present invention offers a broad range of advantages both to contemporary diagnostic procedure as in the ability to rapidly assess kidney function, as well as to the prospective activities associated with the emerging diagnostic and therapeutic role that is envisioned for aminoguanidine and its analogs. The speed, simplicity, accuracy and reliability of the assay of the present invention, make it an excellent diagnostic and research tool that will achieve broad acceptance and utility.

Accordingly, it is a principal object of the present invention to provide a method for measuring the disposition of aminoguanidine and its analogs in tissues and biological fluids.

It is a further object of the present invention to provide a method as aforesaid that may be performed in a facile and inexpensive manner.

It is a yet further object of the present invention to provide a method as aforesaid that may be used as an assay for drugs and other compounds that possess the same activity as aminoguanidine, as well as its metabolites and analogs.

It is a still further object of the present invention to provide an accurate and reliable method for assessing kidney function.

A still further object of the present invention is to provide test kits for the performance of the methods disclosed herein that are simple to use.

A still further object of the present invention is to monitor the effectiveness of a drug regime or like protocol on a mammal having a pathological state or condition related to the presence, activity or elimination of aminoguanidine or its analogs.

Other objects and advantages will become apparent to those skilled in the art from a review of the ensuing description which proceeds with reference to the following illustrative drawings.

BRIEF DESCRIPTION OF THE DRAWINGS

FIG. 2(a–c) comprises individual chromatograms of blank human plasma, a low concentration (0.1 $\mu$g/mL) quality control sample and a high concentration (8 $\mu$g/mL) quality control sample, respectively.

FIG. 4(a–c) comprises individual chromatograms of blank human urine, a low concentration (1.0 $\mu$g/mL) quality control sample and a high concentration (90 $\mu$g/mL) quality control sample, respectively.

DETAILED DESCRIPTION

Accordingly, the present invention related to a method and associated materials for measuring aminoguanidine and its analogs in body fluids and tissues. The method of the present invention comprises:

A. gathering a biological sample believed to contain a quantity of aminoguanidine or analogs thereof;

B. treating the biological sample to deproteinize the biological sample;

C. reacting the deproteinized biological sample of Step B with a pyridine aldehyde in an amount sufficient to convert any aminoguanidine or analogs thereof present in said biological sample to the corresponding pyridinealdehyde-substituted hydrazone;

D. isolating any substituted hydrazone formed in Step C from the remainder of the reaction mixture by high pressure liquid chromatography employing isocratic elution; and E. examining the isolate of Step D to assess the quantity and disposition of said aminoguanidine and/or its analogs.

As mentioned earlier, the present method seeks to offer an assay procedure that is capable of use on an automated, batch-wise basis for both diagnostic and experimental, as well as therapeutic purposes. While the known assay for aminoguanidine as disclosed by Beaven et al. comprises a colorimetric assay, the present method is distinguishing in the formation of the pyridine aldehyde-substituted hydrazone which offers ultraviolet detection and, more importantly, stability and corresponding accuracy and reproduceability of results. The formation of hydrazones is itself not new, having been disclosed by Ceba et al., "Analytical Properties of Pyridine-2-Aldehyde Guanylhydrazone," TALANTA 28:134-136 (1981). The authors disclosed the preparation of the hydrazone and suggested its utility as an analytical reagent with a variety of inorganic cations because it forms distinctly visible complexation products with them. Nothing in the Ceba et al. article suggests that aminoguanidine may be assayed by the reaction to form the corresponding guanylhydrazone and that the resulting reaction product would be distinctly detectable in the ultraviolet range at 302 nanometers.

As mentioned earlier, the deproteinization of the sample may be accomplished by treating the sample with an agent capable of precipitating protein, or by subjecting the sample to other separation techniques such as ultrafiltration. Suitable agents may be selected from the group consisting of moderate to strong acids, such as perchloric acid and trichloroacetic acid, with the latter being preferred. In the event that trichloroacetic acid is used, an exemplary concentration is 7.5 percent. Agents may also be selected from the group consisting of organic solvents used in solvent-based protein precipitation procedures, such as methanol, acetonitrile and methylene chloride. The techniques of protein precipitation are well-known and alternate procedures are contemplated herein. Accordingly, the agents and procedures specified herein are presented for purposes of illustration and in compliance with Applicants' duty to present a best mode for the practice of this invention.

The pyridine aldehyde useful in the present invention may comprise 6-methyl picolinaldehyde which may, for example, be prepared to a concentration of 10 mg/ml in solution. Also, the reaction between the pyridine aldehyde and the deproteinized biological sample should preferably take place under mildly acidic conditions. The selection of a particular pyridine aldehyde and a particular concentration may vary, however, within the skill of the art, and, accordingly, the above is likewise presented for purposes of fulfilling Applicants' duty to disclose the best mode of carrying forth the invention.

In the next step of the present method, any substituted hydrazone that may be formed from the reaction between the biological sample and the pyridine aldehyde is then isolated from the remainder of the reaction mixture by high pressure liquid chromatography employing either an isocratic or a gradient elution. More particularly, the chromatographic protocol may utilize a radial compression chromatographic column with an isocratic flow rate under paired-ion conditions. Any resulting hydrazone isolate may then be examined by ultraviolet spectroscopy, and, in particular, in the instance of aminoguanidine, would be detectable at a wavelength of about 302 nanometers. The specificity of this detection is one of the advantageous features of the present invention and distinguishes the colorimetric assays already known in the art.

The practice of the present method includes reference to an internal standard which is preferably combined with the biological sample prior to its treatment in accordance with step B) of the present method. The internal standard is chosen to have similar structural and functional properties so that procedural controls over the method may be maintained. Suitable compounds useful as the internal standard comprise aminoguanidine and its analogs. Thus, the internal standard may comprise aminoguanidine or an analog such as N-ethyl aminoguanidine (=N-ethylhydrazine carboximidamide). Naturally, the present invention is not limited to the use of a particular compound as an internal standard, and contemplates other compatible compounds with structural and functional similarities to aminoguanidine within its scope.

As mentioned earlier, the present method possesses numerous applications, among them the measurement and detection of aminoguanidine and its analogs in a variety of biological environments. Specifically, the biological samples that may be measured in accordance herewith include fluids such as plasma, saliva, urine, and tissue. Likewise, the present method possesses numerous diagnostic and therapeutic uses.

Accordingly, in a further embodiment, the present invention relates to a method for monitoring the efficacy of a therapeutic protocol or drug therapy involving the administration of a compound such as aminoguanidine or its analogs, for example, to combat the deleterious effects of the advanced glycosylation of body proteins, as is evidenced in the aging process and in diabetes. The present method may thus be performed by the isolation and examination of biological samples taken from plasma, urine or tissue. Plasma samples may be tested to determine whether therapeutically sufficient levels of aminoguanidine are present in the blood, while urine samples may be assayed to determine the rate of aminoguanidine clearance, to determine the rate at which corresponding administration of aminoguanidine must take place to maintain effective therapeutic levels. Finally, tissue samples may be taken from the organs or areas of the body targeted for therapy to determine whether sufficient quantities of the therapeutic agent are being delivered to that area.

Accordingly, the present invention extends to a method for treating patients to inhibit the formation of advanced glycosylation end products in the body, comprising the administration of an effective amount of an inhibitor of such advanced glycosylation, including a compound selected from the group consisting of aminoguanidine and its analogs thereof, further including continuous monitoring whether therapeutically effective levels of aminoguanidine or its analogs are present in biological samples taken from the subject, including body fluids and tissues. In such instance, the present assay method may be conducted at regular intervals, the exact intervals varying in accordance with the individual administrative protocol and patient profile. For example, such intervals may range from one hour to 24 hours.

The present invention is applicable to the detection and measurement of analogs of aminoguanidine as noted earlier, and in this connection, extends to a drug screening assay for the identification of compounds that may inhibit the formation of advanced glycosylation end products and which may bear some structural analogy to aminoguanidine. In such event, a biological sample such as a tissue sample or cell culture may be incubated with a quantity of the compound under test, and thereafter, the present assay may be conducted to determine the presence and activity of the compound under observation and to thereby determine its absorption, distribution, metabolism and/or excretion profile. In the instance where clinical trials of a prospective inhibitor compound having structural analogy to aminoguanidine are in progress, the new drug may be administered to subjects and urine samples may be taken at regular intervals to determine the extent to which the drug is detected and its renal clearance takes place. Such test may be conducted as an adjunct to the testing of tissue and plasma samples, to determine not only the efficacy of the new drug but to attempt to formulate an appropriate administrative protocol.

The present invention likewise extends to a test kit for the performance of the assay for aminoguanidine and its analogs, which comprises:

A. a quantity of an agent for use in deproteinization of the biological sample;

B. a quantity of a pyridine aldehyde for reaction with available aminoguanidine or analog compounds;

C. other reagents and substrates used in high pressure liquid chromatography; and D. directions for use of the kit.

The choice of deproteinization agents and pyridine aldehydes useful in the present test kit may be as described earlier herein Likewise, the kit may include a quantity of an internal standard as described earlier, as well as the reagents and materials generally used in high pressure liquid chromatography.

A further embodiment of the present invention extends to a method for measuring kidney function comprising administering to a subject a predetermined quantity or dose of a primary reagent selected from the group consisting of aminoguanidine and its analogs, collecting plasma samples from the subject at regular intervals and examining the samples for the content and disposition of the said aminoguanidine or analog thereof This method broadly contemplates the use of aminoguanidine and its analogs as a primary reagent for this purpose, and extends to various testing protocols in which such a reagent may be administered and then monitored and/or measured. Particular variations in protocol are accordingly encompassed herein, and a test kit is likewise contemplated which comprises a quantity of a primary reagent selected from aminoguanidine and its analogs, other reagents and substrates, and directions for use of the kit.

A particular method for measuring kidney function is disclosed which comprises the measurement of the elimination half-life ($T_{\frac{1}{2}}$) of aminoguanidine or its analogs and the comparison of these data to a continuum of such data developed from a variety of reference individuals. More particularly, the method comprises administering a fixed dose of aminoguanidine or an analog thereof, collecting plasma samples from the subject at regular intervals, examining the samples by the present assay method and determining from the results the elimination half-life data for each of the samples, and comparing these data with a predetermined continuum of data gained from the testing and analysis of individuals with a variety of kidney function. The data determined include both elimination half-life and Glomerular Filtration Rate (GFR). These individual data are combined to define a ratio from which either a tabular or graphical data continuum may be expressed.

By way of background, the measurement of kidney function has long been considered an important indicator in the assessment of general health as well as particular pathologies such as nephropathy. Renal decline or failure independent of pathology is critical because of the equally vital function that the kidneys play in the respiratory and metabolic activity of the body. For example, kidney failure would necessitate either hemodialysis or kidney transplantation. In the instance of the former, kidney function must be continually monitored to determine the necessity or frequency of dialysis treatment. It can therefore be appreciated that kidney failure may or may not be the result of diabetes. The method described here is of general use in assessing kidney function in any pathological condition.

Several procedures are known for the measurement of kidney function, among them the intravenous infusion of radioactive tracers. The tracer is first administered and thereafter blood samples and quantitative urine samples are taken to determine the renal clearance of the tracer under steady-state conditions. Although this technique is accurate, it has several drawbacks, among them, the need for careful patient supervision and timing with regard to the collection of urine and blood samples. Likewise, the radioactive materials that must be administered to the patients represent safety hazards to personnel as well as the attendant problems of storage and shipment of isotopes and the expense of purchase and replacement of such isotopes due to their short half-life, as well as safety and financial considerations. Thus, the short half-life of the radioisotopes involves results in the frequent replacement, in many instances, prior to use of the material, as well as the attendant contamination of facilities, patients and personnel involved in the administration of the material in the assay.

A second method involves the measurement of endogenous creatinine clearance. In this method, both blood and complete urine samples must be collected from the patient, and inaccuracies result mainly in the difficulty in obtaining complete urine collections. Many patients for whom kidney function determinations are desired exhibit neurologic impairment that makes complete emptying of the bladder difficult, if not impossible. Moreover, 24-hour urine collections require patient compliance to collect all urine, at home or even in the hospital setting, so that compliance by the patient cannot be assured. Accordingly, although creatinine clearance determination is scientifically sound and theoretically accurate, it often fails in the practical aspects of obtaining accurate samples for examination.

By contrast with the above, the present methodology as applied to kidney function determinations provides a simple, convenient and reliable protocol All that is necessary is for a single, small dose of aminoguanidine to be administered and for three blood collections to be taken. The administration of the small dose of aminoguanidine represents a low risk, and the reduced number of fluid collections likewise reduces risk and inconvenience to the patient. As will be shown hereinafter, information obtained from the performance of the present assay as applied to kidney function assessment indicates that there is an excellent linear correlation between aminoguanidine half-life and kidney function as determined by Glomerular Filtration Rate.

As mentioned earlier, the performance of the particular embodiment of the present method for assessing kidney function comprises the following steps:

A) A single 300 mg dose of aminoguanidine hydrochloride is administered to the patient. Administration may be either by a capsule or tablet taken orally, or by a liquid syrup, elixir or the like.

B) After administration of the aminoguanidine or analog material, periodic collection of plasma samples is then conducted. For example, minimum 3 ml blood samples may be collected, and in the instance where aminoguanidine is administered in dry form as in a pill, the first sample may be taken 10 hours after ingestion, the second sample may be taken 14 hours after ingestion, and the third sample may be taken 18 hours after ingestion. In the instance where a liquid is administered, a similar regimen may be observed.

C) The samples collected at the intervals indicated may then be processed in accordance with the method of the present invention to determine aminoguanidine concentration.

D) Thereafter, the elimination half-life ($T_{\frac{1}{2}}$) may be determined. Particularly, the data may be interpreted and determined by reference to the relationship wherein the slope of the logarithmic decline of plasma concentration over time is identified as the elimination rate ($K_{elim}$). Elimination half-life ($T_{\frac{1}{2}}$) is related to $K_{elim}$ by the following equation:

$$T_{\frac{1}{2}} = \frac{0.6931}{K_{elim}}$$

E) After determining the aminoguanidine elimination half-life, it may then be compared with a continuum which relates the elimination half-life aminoguanidine to kidney function values from a large number of individuals with a variety of kidney functions, from normal to poor, on whom both measurements have been made. This existing data base or continuum displays an inverse relationship between aminoguanidine half-life and the Glomerular Filtration Rate (GFR).

Based upon presently available data and experimentation wherein 300 mg oral dosages of aminoguanidine hydrochloride have been administered and assayed, a relationship between $T_{\frac{1}{2}}$ and GFR has been developed. The relationship is as follows aminoguanidine $T_{\frac{1}{2}} = -0.14$ (GFR) $+ 22.04$ (r = 0.875; n = 18)

The foregoing relationship may be solved for Glomerular Filtration Rate and the resulting data points may be compared with a continuum of data points established from the testing of individuals with known kidney function. A representative such continuum is presented in FIG. 5 hereof, which comprises a graphical plot of aminoguanidine half-life $T_{\frac{1}{2}}$ against GFR and includes data developed and presented in Example 3 later on herein.

As mentioned earlier, one of the advantages of the present method is the independence from the inaccuracies and inconvenience of urine collection and examination. The present method may be utilized by simple administration of the predetermined quantity of aminoguanidine followed by the collection of plasma samples at the regular intervals such as those proposed above. The samples may then be processed in accordance with the present method and the resulting data transposed into corresponding elimination data for aminoguanidine which may be compared with the pre-existing continuum of data by either graphical or tabular means. In this fashion, a safe, effective and simple method for monitoring kidney function is available, which would extend to the detection of the onset or presence of pathologies associated with kidney dysfunction, is thereby made available.

In a further aspect of the present invention, a test kit for assessing kidney function in accordance with a preferred embodiment of the invention is disclosed which comprises:

A) a quantity of aminoguanidine or an analog thereof in a premeasured dosage form suitable for administration to a test subject;

B) a graphical or continuum of quotients comprising indices derived from the ratio of the elimination half-life $T_{\frac{1}{2}}$ of aminoguanidine or its analogs to its Glomerular Filtration Rate (GFR);

C) a quantity of an agent for deproteinization of the biological sample;

D) a quantity of a pyridine aldehyde for reaction with available aminoguanidine or analog compounds;

E) other reagents and substrates used in high pressure liquid chromatography; and F) directions for use of the kit.

As with the test kit described earlier, the present test kit may include an internal standard such as an aminoguanidine or an analog thereof. Likewise, the reagents used in the test kit may comprise those reagents including the deproteinizing agents indicated earlier. The test kit may be prepared for use on a repetitive basis, in which event certain of the consumable aspects of the kit can be provided in multiple dosage quantities; or the kit can be prepared for one-time usage wherein specific quantities of each reagent and consumable element will be provided.

Likewise, certain of the reagents may be prepared in dried form such as by lyophilization, so that the kit may be easily packaged and provided in dry form with specific instructions for the addition of suitable liquid to activate the reagents for use.

The predetermined or premeasured quantity of aminoguanidine or its analogs to be used in the present test kit may be prepared in a variety of ways for administration. Preferably, the dosage form may be prepared for oral administration, and accordingly both solid and liquid dosage forms are contemplated For example, suitable dosage forms would include tablets, capsules, dragees, candies, syrups, elixirs and the like. While a variety of concentrations of aminoguanidine are useful, and the invention is not limited to a specific concentration thereof, a dosage form of 300 mg of aminoguanidine hydrochloride or an analog thereof has been utilized and is presently preferred.

The present invention will be better understood from a review of the following illustrative examples.

EXAMPLE 1

The following experiments were performed to determine the accuracy of the present method in examination of plasma samples from a variety of mammals. Accordingly, samples were gathered from rats, dogs and human subjects and were inoculated with predetermined quantities of aminoguanidine. Two analysts performed separate and parallel assays to assess the reproduceability and reliability of the present assay procedure. The resulting samples of each analyst were then processed as described below.

Analytical Method

1. Sample Preparation

To a 0.5 mL plasma sample was added 0.5 mL of the working internal standard solution (10 μg/mL N-ethyl aminoguanidine tosylate in 7.5% trichloracetic acid). After vortexing (10 sec.) and centrifugation in a microfuge (Eppendorf, 14,000 rpm, 10 min.), the supernatant was decanted into a clean screw top culture tube containing 0.1 mL of an aqueous (10 mg/mL) solution of reacting agent (6-methyl-2-pyridine-carboxaldehyde). The sample was then capped tightly and reacted in a heating block (95°-100° C.) for 10 minutes. After cooling, i the sample was transferred into an HPLC vial, from which a 200 μL aliquot was injected for HPLC analysis.

2. Chromatography

A Waters Associates Model 510 pump was utilized with a radial compression column (Waters Novapak CN, 8 mm × 10 cm, 4 μm particle size) and a cyano (Waters Resolve Guard-Pak CN) precolumn. Detection was performed using a variable ultraviolet detector (Waters 484) at 302 nm. The mobile phase consisted of (volume to volume) 15% acetonitrile: 10% methanol: 75% of 0.01 M each of 1heptanesulfonic acid and sodium phosphate monobasic. Flow rate was maintained isocratically at 2.0 mL/min. at ambient temperature. Sequential automatic injections were made via a programmable sampler (Waters WISP 712).

3. Data Analysis

All data acquisitions were performed with a Waters Maxima 820 system. A linear test squares analysis of the ratios of drug peak height to internal standard peak height versus concentrations added to human plasma in standards constituted daily instrumentation standardization. Interpolation from the linear regression line determined concentrations of aminoguanidine in quality control and unknown assayed samples

Results and Discussion

Figure 1:
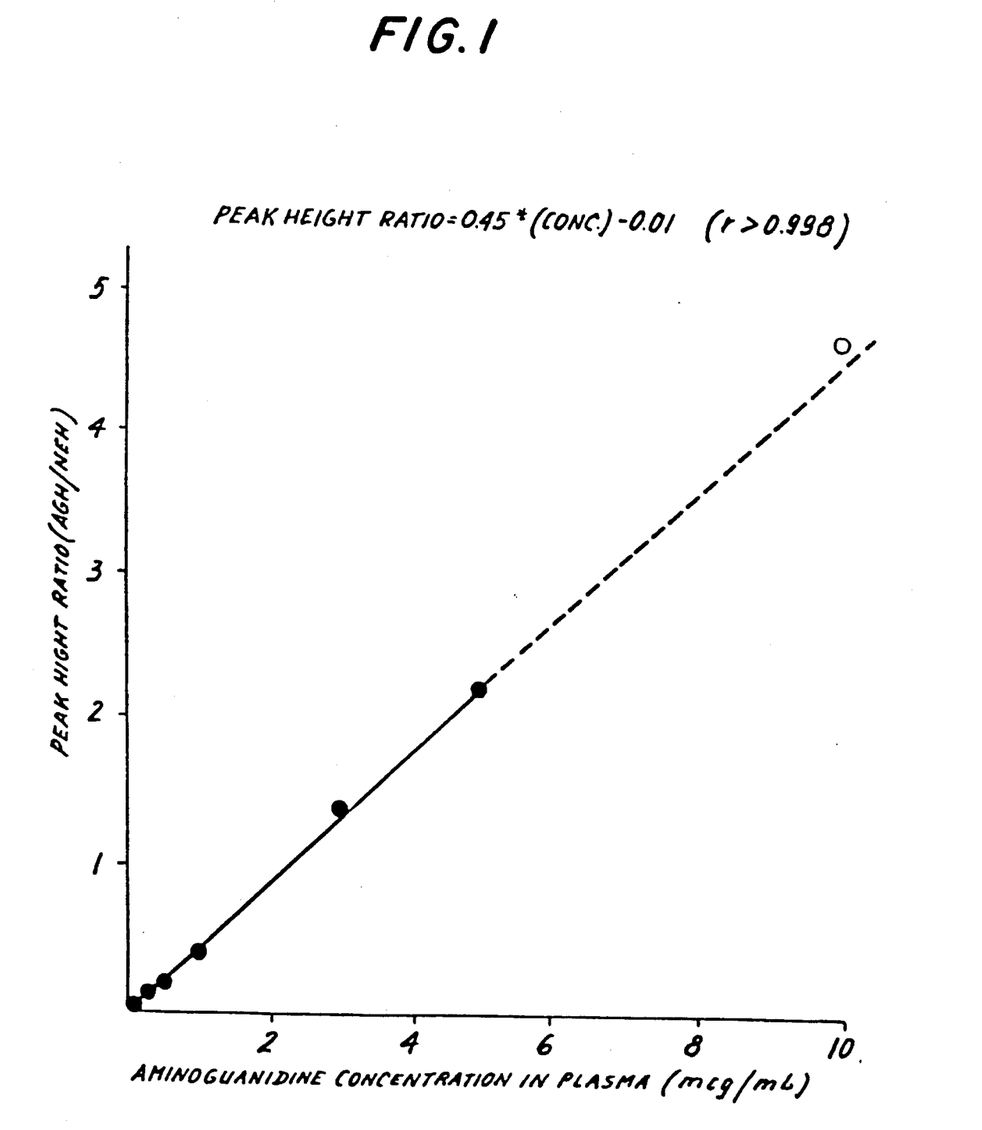
FIG. 1 is a graph of the summary of the standard curve data derived from the performance of the assay with the plasma of rats, dogs and humans.

On a daily basis, linearity ($r > 0.998$, $p < 0.01$) was observed over the concentration range of 0–10 μg/mL of free aminoguanidine, with the lowest standard (0.05 μg/mL) being consistently detectable. FIG. 1 summarizes the standard curve data from this study, and shows the plot of mean peak height ratio responses versus plasma concentration. The standard curve data from the two analysts in this study were essentially superimposable and the overall mean data were accordingly plotted.

Figure 2:
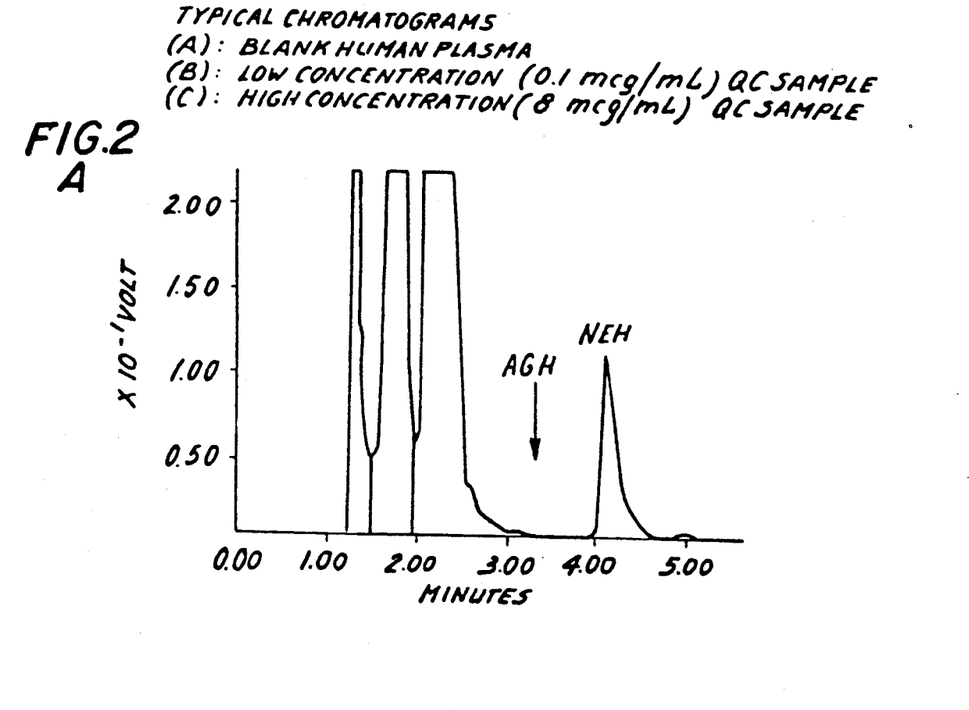
Figure 2C:
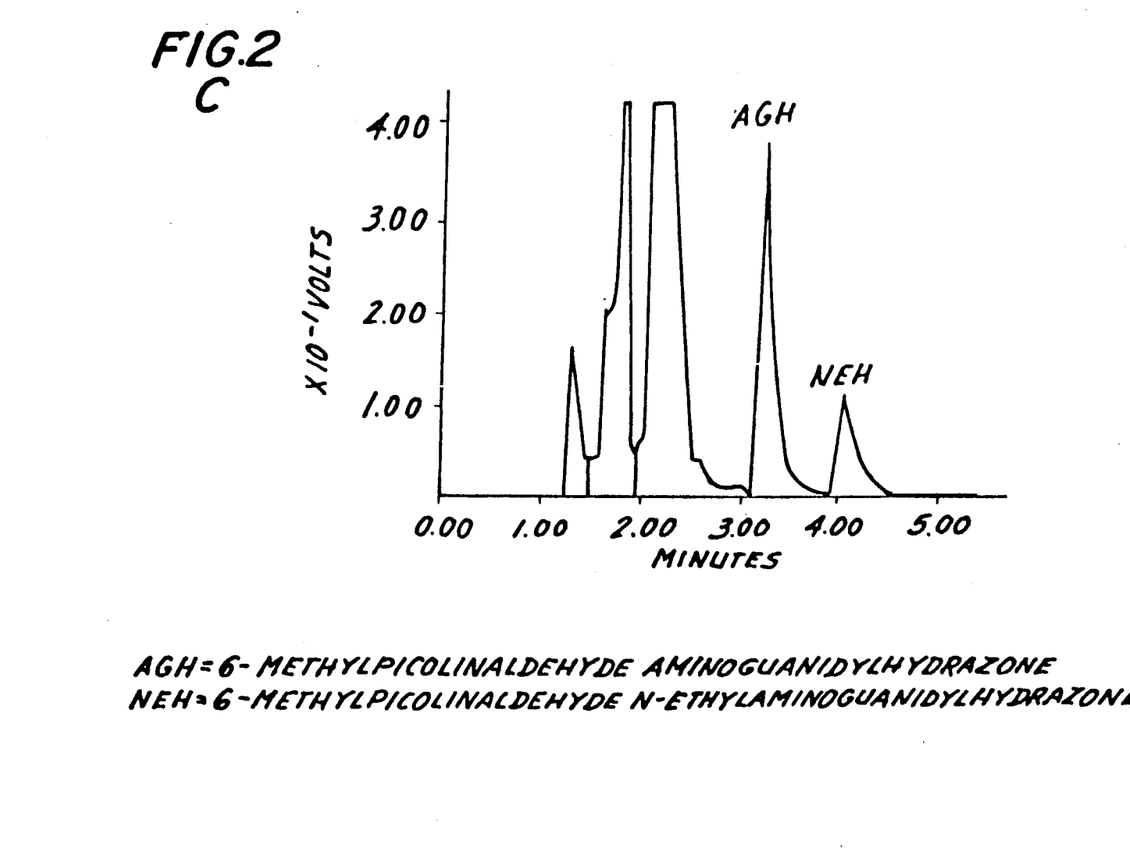

From a chromatographic perspective, 6-methyl-picolinaldehyde guanylhydrazone (AGH) and 6-methyl picolinaldehyde-N-ethyl guanylhydrazone (NEH), the two adducts formed during reaction with picolinaldehyde (6-methyl-2-pyridine-carboxaldehyde), were adequately resolved from each other and from endogenous interferences. FIG. 2 shows chromatograms of blank human plasma, a low concentration (0.1 μg/mL) quality control sample and a high concentration (8 μg/mL) quality control sample.

There were apparently minor differences over time on each run, as shown by the pre-quality control run of the standard curve versus the post-quality control run of the standard curve (data not shown). The reason(s) for these changes may be attributable to organic solvent partitioning to various levels of the mobile phase (chromatography was done without mobile phase stirring) or they may be due to temperature fluctuations during overnight runs. In actual analyses of real bioanalytical samples, however, these problems would be obviated by interspersing standards and quality control samples throughout the run with slow, continuous stirring of the mobile phase. For this study, therefore, a regression analysis through all the standard points (pre- and post-quality control) would adequately simulate results from a randomly interspersed standard curve.

The plasma quality control samples for all three groups tested (0.1, 0.8, 2.0 and 8.0 μg/mL of free aminoguanidine respectively, for quality control samples A-D) are summarized in Table I, below.

TABLE I

BIOANALYTICAL VALIDATION DATA FROM HPLC ASSAY FOR THE DETERMINATION OF AMINOGUANIDINE IN PLASMA

| SAMPLE | Aminoguanidine in Plasma | | | | | | | |
|---|---|---|---|---|---|---|---|---|
| | QC*-A | | QC*-B | | QC*-C | | QC*-D | |
| Conc. | 1.0 μg/ml | % Diff. | 8.0 μg/ml | % Diff. | 2 μg/ml | % Diff. | 8 μg/ml | % Diff. |
| HUMAN PLASMA | | | | | | | | |
| mean | 0.10 | −5.0 | 0.75 | −5.8 | 1.98 | −0.9 | 7.79 | −2.6 |
| s.d. | 0.01 | | 0.04 | | | | | |
| n | 22 | | 24 | | | | | |
| C.V. (%) | 12.9 | | 5.7 | | | | | |
| DOG PLASMA | | | | | | | | |
| mean | 0.9 | 1.8 | 0.74 | −7.0 | 2.01 | 0.6 | 7.54 | −5.7 |
| s.d. | 0.01 | | 0.06 | | 0.20 | | 0.75 | |

TABLE I-continued
BIOANALYTICAL VALIDATION DATA FROM HPLC ASSAY FOR THE DETERMINATION OF AMINOGUANIDINE IN PLASMA Aminoguanidine in Plasma

| SAMPLE | QC*-A | | QC*-B | | QC*-C | | QC*-D | |
|---|---|---|---|---|---|---|---|---|
| Conc. | 1.0 µg/ml | % Diff. | 8.0 µg/ml | % Diff. | 2 µg/ml | % Diff. | 8 µg/ml | % Diff. |
| n | 11 | | 12 | | 12 | | 12 | |
| C.V. (%) | 10.6 | | 8.2 | | 10.1 | | 9.9 | |
| RAT PLASMA | | | | | | | | |
| mean | 0.11 | 9.1 | 0.77 | −3.2 | 2.08 | 4.0 | 7.70 | −3.8 |
| s.d. | 0.01 | | 0.05 | | 0.12 | | 0.69 | |
| n | 11 | | 12 | | 12 | | 12 | |
| C.V. (%) | 13.3 | | 6.9 | | 5.6 | | 8.9 | |

% Diff. = 100% * (obs.conc − theor.conc)/(theor.conc)
QC = Quality Control

Referring to Table I, the precision of the human plasma assay, as measured by the coefficients of variation (C.V., in percent), ranged from 3.6% to 12.9% (overall mean=6.5%) over the concentration range studied (0.1–8 µg/mL). Accuracy, as measured by the percent difference from theoretical concentrations, ranged from −0.9% to −5.8% (overall mean=3.6%), which is quite acceptable from a bioanalytical standpoint.

The animal plasma quality control (both dog and rat) samples were made up daily by spiking aqueous aminoguanidine solutions into blank animal plasma. This was done to evaluate the feasibility of assaying samples from small animal studies in which making up a large quantity of plasma standards would not be desirable.

With respect to the precision of the assay as to the dog plasma quality control samples, there was an overall mean coefficient of variation of 9.7% (range: 8.2% to 10.6%). In terms of accuracy, the overall mean percent different from the theoretical concentration was −2.6% (range: −7.0% to 1.8%).

The precision of the assay as to the rat plasma quality control samples averaged 8.7% C.V. (range: 5.6% to 13.3%) and overall mean percent difference from theoretical concentrations was 1.5% (range: −3.8% to 9.1%).

Under current assay conditions, plasma samples whose assayed free aminoguanidine concentration exceed 10 µg/mL should be diluted with blank human (or appropriate animal) plasma and reassayed to bring the samples' responses to within the linearity range of the standard curve (0.05–10 µg/mL). Samples whose interpolated aminoguanidine concentrations are less than 0.05 µg/mL should be designated as "NR" (Not Reportable) and treated as zeros in further calculations (i.e., pharmacokinetics, statistics, etc.).

The results of this study indicate that the developed HPLC assay is reproducible, accurate and rugged. Overall mean coefficients of variation (precision) for all three species of plasma were less than 10% and overall mean accuracies were within 4% of theoretical concentrations. Assay ruggedness was well characterized by excellent results from two analysts over a three-day validation period, in which the detectable adducts appear to be stable for well over a day, thereby facilitating batch mode sample processing and high throughput analyses Animal plasma can be successfully assayed for aminoguanidine concentrations utilizing a human plasma standard curve. Future analyst(s) undergoing this validation procedure are expected to attain 10% precision and 5% accuracy criteria.

In summary, the present assay was satisfactorily validated in human, dog and rat plasma.

EXAMPLE 2

This experiment was designed and conducted in similar fashion to Example 1, to confirm the accuracy and operability of the present assay with urine samples. Two analysts, using one HPLC system, independently prepared a human urine standard curve and quadruplicate analyses of four known quality control samples for HPLC analysis each day for two days to characterized assay performance specifications.

Analytical Method

1. Sample Preparation

To a 0.5 mL urine sample (or standard or Q.C. sample) was added 0.5 mL of the working internal standard solution (10 µg/mL N-ethyl aminoguanidine tosylate in 7.5% trichloracetic acid) and 0.5 mL of an aqueous (10 mg/mL) solution of reacting agent (6-methyl-2-pyridinecarboxaldehyde) in a clean screw-top culture tube. The samples were capped tightly, vortexed (10 sec.) and reacted in a heating block (95°–100° C.) for 10 minutes. After cooling, the sample was transferred into a HPLC vial, from which a 50 µL aliquot was injected for HPLC analysis.

2. Chromatography

A Waters Associates Model 510 pump was utilized with a radial compression column (Waters Novapak CN, 8 mm ×10 cm, 4 µm particle size) and a cyano (Waters Resolve Guard-Pak CN) precolumn. Sample components were detected using a variable ultraviolet detector (Waters 484) at 302 nm. The mobile phase consisted of (volume to volume) 10% acetonitrile: 10% methanol: 80% of 0.01 M each of 1-heptanesulfonic acid and monobasic sodium phosphate. Organic solvent partitioning was avoided by the slow stirring of the mobile phase with a magnetic stirrer throughout the run. Flow rate was maintained isocratically at 2.0 mL/min. at ambient temperature. Sequential automatic injections were made via a programmable sampler (Waters WISP 712).

3. Data Analysis

All data was acquired with a Waters Maxima 820 chromatography workstation. A linear test squares analysis by the analysts of the ratios of drug peak height to internal standard peak height versus concentrations added to human urine in standards constituted daily instrumentation standardization. Interpolation from the linear regression line determined concentrations of aminoguanidine in quality control and unknown assayed samples.

Results and Discussion

Figure 3:
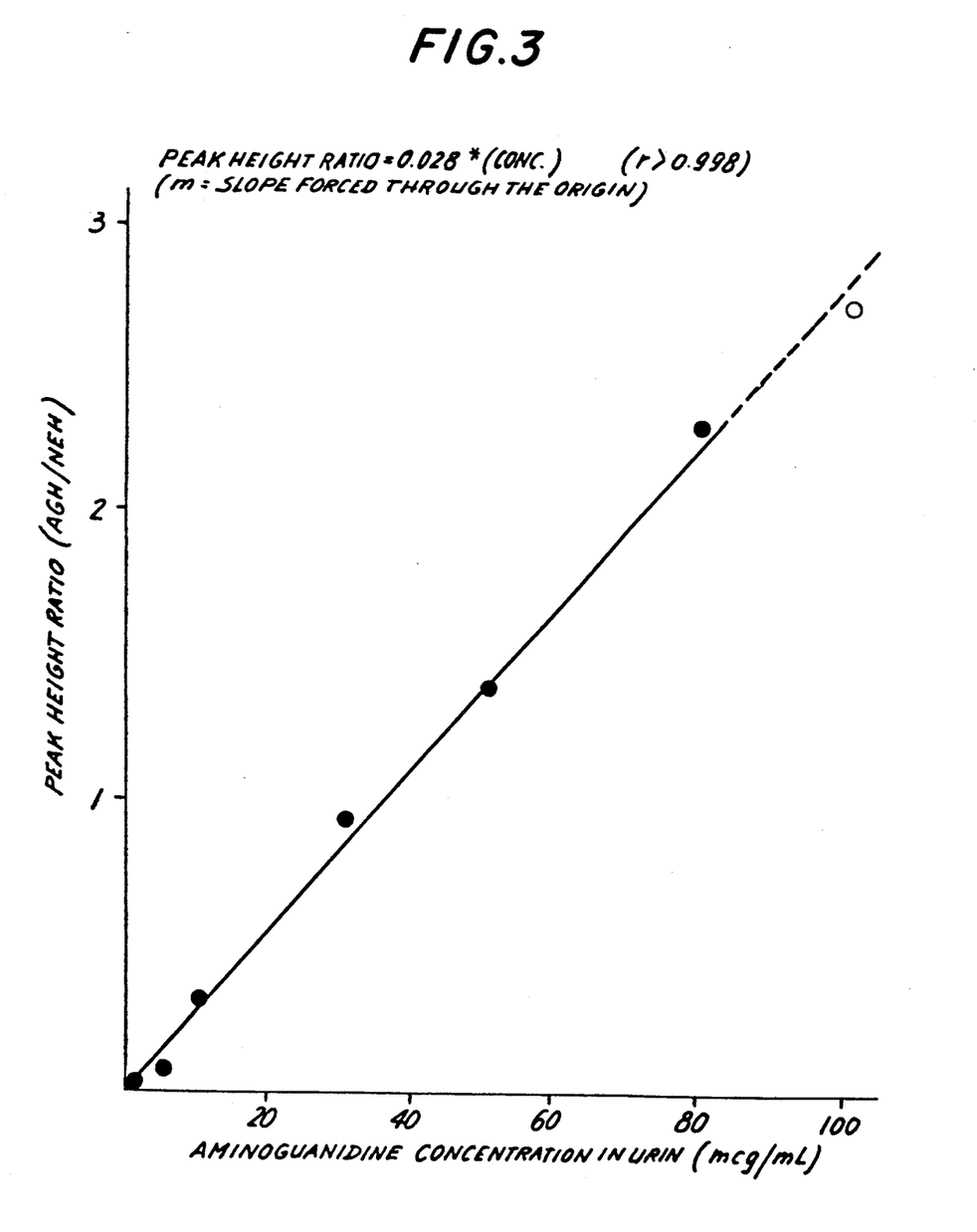
FIG. 3 is a graph of the summary of the standard curve data derived from the performance of the assay with human urine.

On a daily basis, linearity ($r > 0.998$, $p < 0.01$) was observed over the concentration range of 0–100 μg/mL of free aminoguanidine, with the lowest standard (0.5 μg/mL) being consistently detectable. FIG. 3 summarizes the standard curve data from this study and shows the plot of mean peak height ratio responses versus plasma concentration. As with Example 1, the standard curve data from the two analysts in this study are essentially superimposable, and the overall mean data were therefore plotted.

Figure 4A:
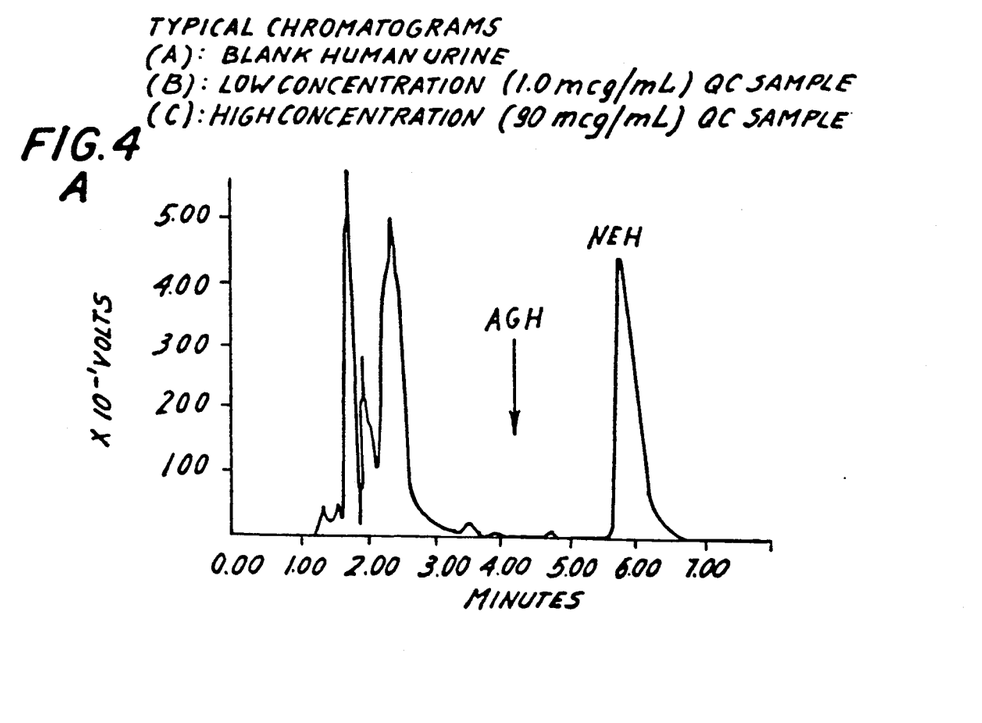
Figure 4B:
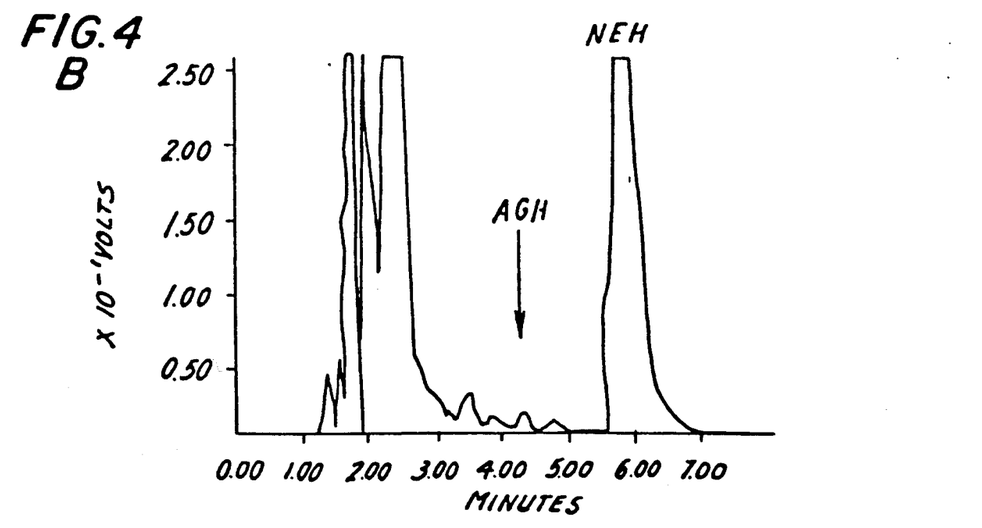
Figure 4C:
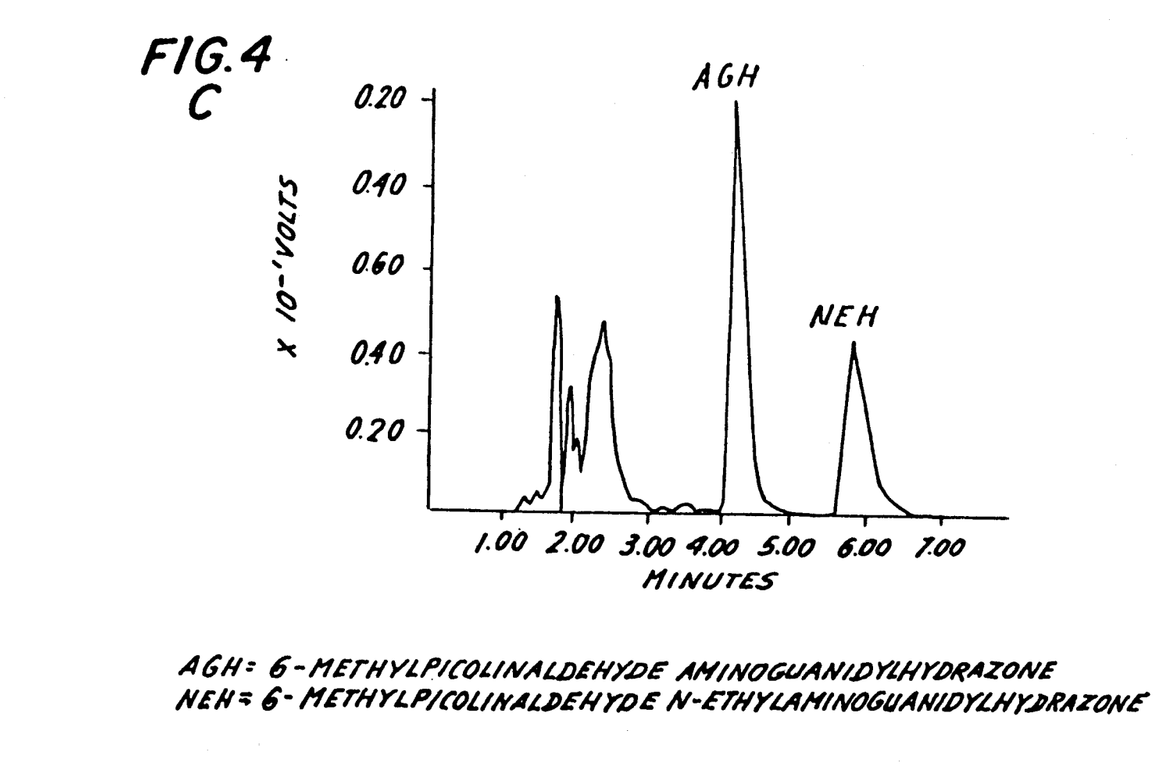

From a chromatographic perspective, 6-methylpicolinaldehyde guanylhydrazone (AGH) and 6-methyl picolinaldehyde-N-ethyl guanylhydrazone (NEH), the two adducts formed during reaction with picolinaldehyde (6-methyl-2-pyridine-carboxaldehyde) were adequately resolved from each other and from endogenous interferences. FIG. 4 shows chromatograms of blank human urine, a low concentration (1.0 μg/mL) quality control sample and a high concentration (90 μg/mL) quality control sample.

As with the assay results of Example 1, minor differences over time were noted on each run, as shown by the prequality control run of the standard curve versus the post-quality control run of the standard curve (data not shown). The reason(s) for these changes may be due to temperature fluctuations in the laboratory during overnight runs. These potential temperature fluctuations had the greatest effect on retention time. However, the peaks of interest were still sufficiently resolved from one another and other extraneous peaks that they were easily detected and integrated. As with Example 1, these problems would be averaged by interspersing standards and quality control samples throughout the run, and for this study therefore, a regression analysis through all standard points would adequately simulate results.

The human urine quality control samples (1.0, 8.0, 40 and 90 μg/mL of free aminoguanidine respectively, for quality control samples A-D) are summarized in Table II, below.

$-6.7\%$ to $15.5\%$ (overall mean $= 4.8\%$), which is quite acceptable from a bioanalytical standpoint.

Under current assay conditions, urine samples whose assayed free aminoguanidine concentration exceeds 100 μg/mL should be diluted with blank human (or appropriate animal) urine and reassayed to bring the samples, responses to within the linearity range of the standard curve (0.5–100 μg/mL). Samples whose interpolated aminoguanidine concentrations are less than 0.5 μg/mL should be designated as "NR" (Not Reportable) and treated as zeros in further calculations (i.e., pharmacokinetics, statistics, etc.).

The results of this study further confirm that the present assay is reproducible, accurate and rugged and is useful with urine samples. The overall mean coefficient of variation (precision) for human urine was less than 5% and the overall mean accuracy was within 5% of theoretical concentrations. Assay ruggedness was well characterized by excellent results from two analysts over a two-day validation period, in which the detectable adducts appear to be stable for well over a day, thereby facilitating batch mode sample processing and high throughput analyses. Future analyst(s) undergoing this validation procedure are expected to attain 5% precision and 5% accuracy criteria.

EXAMPLE 3

To illustrate the use of the present method in the measurement of kidney function, a group of 19 test subjects were given a total dosage of 300 mg of aminoguanidine hydrochloride. After administration of this total dosage, plasma samples were collected from each of the patients at intervals of 10 hours, 14 hours and 18 hours after administration. The plasma samples were then taken and subjected to the assay of the present invention, in accordance with the protocol utilized in Example 1.

Accordingly, the samples were first combined with a quantity of a working internal standard solution of N-ethyl aminoguanidine tosylate in 7.5 percent trichloroacetic acid. The resulting samples were vortexed for 10 seconds and centrifuged for a period of 10 minutes at a speed of 14,000 rpm. The supernatants were then decanted into a culture tube containing 0 1 ml of an aque-

TABLE II

BIOANALYTICAL VALIDATION DATA FROM HPLC ASSAY FOR
THE DETERMINATION OF AMINOGUANIDINE IN HUMAN URINE
Aminoguanidine in Human Urine

| SAMPLE Conc. | QC*-A | | QC*-B | | QC*-C | | QC*-D | |
|---|---|---|---|---|---|---|---|---|
| | 1.0 μg/ml | % Diff. | 8.0 μg/ml | % Diff. | 40 μg/ml | % Diff. | 90 μg/ml | % Diff. |
| HUMAN PLASMA | | | | | | | | |
| mean | 1.0 | 3.1 | 9.2 | 15.5 | 42.9 | 7.2 | 83.9 | −6.7 |
| s.d. | 0.1 | | 0.6 | | 2.0 | | 1.5 | |
| n | 16 | | 16 | | 16 | | 16 | |
| C.V. (%) | 6.8 | | 6.3 | | 4.6 | | 1.8 | |

% Diff. = 100% * (obs.conc − theor.conc)/(theor.conc)
QC = Quality Control

Quality control concentrations were calculated using m' (regression slope forced through the origin, $n = 14$) to obtain the greatest accuracy. All results shown used m' to determine "unknown" concentrations. Precision, as measured by the coefficients of variation (C.V., in percent), ranged from 1.8% to 6.8% (overall mean $= 4.9\%$) over the concentration range studied (1.0–40 μg/mL). Accuracy, as measured by the percent difference from theoretical concentrations, ranged from ous solution (10 μg/ml) of 6-methyl picolinaldehyde. The samples were then tightly capped and reacted in a heating block for a period of 10 minutes, and after cooling, were transferred into HPLC vials from which aliquots were then injected for HPLC analysis.

A radial compression chromatographic column was utilized with an isocratic flow rate and under paired-ion conditions. Detection was performed using a variable ultraviolet detector at 302 nanometers, and all data acquisitions were utilized and converted to elimination half-life data by the calculation of the elimination rate by the formula $$T_{\frac{1}{2}} = \frac{0.6931}{K_{elim}}$$

These data were then plotted versus the patients' GFRs measured by radioactive tracer, and the resulting linear relationship between the two used to calculated Glomerular Filtration Rates by the formula $T_{\frac{1}{2}} = -0.14$ GFR + 22.04, (r=0.875 and n=18). Corresponding values for $T_{\frac{1}{2}}$ and GFR were then derived for each of the patients, and these data are presented in Table III, below.

TABLE III

| PATIENT | GFR | AG T½ |
|---|---|---|
| 1 | 12.8 | 24.59 |
| 2 | 52.4 | 14.19 |
| 3 | 116.3 | 3.83 |
| 4 | 44.1 | 21.75 |
| 5 | 31.1 | 19.04 |
| 6 | 80.5 | 6.78 |
| 7 | 26.7 | 14.83 |
| 8 | 12.1 | 24.91 |
| 9 | 117.2 | 4.73 |
| 10 | 148.9 | 3.94 |
| 11 | 111.9 | 6.82 |
| 12 | 103.8 | 6.08 |
| 13 | 41.6 | 14.92 |
| 14 | 39.2 | 9.54 |
| 15 | 113.2 | 4.81 |
| 16 | 82.2 | 6.03 |
| 18 | 131.3 | 7.05 |
| 19 | 131.1 | 6.46 |

Figure 5:
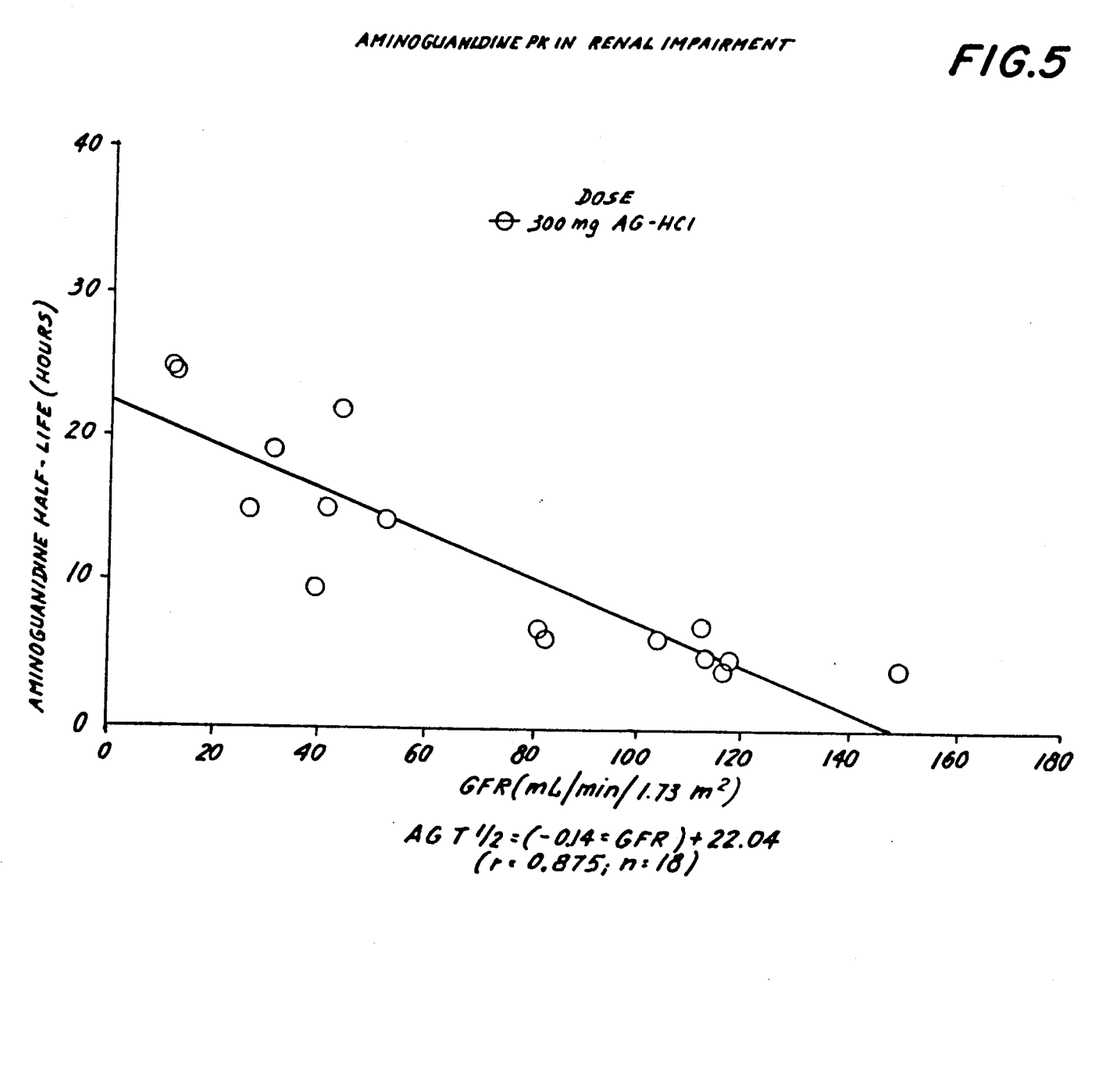
FIG. 5 is a graph of a continuum of quotients of aminoguanidine elimination half-life ($T_{\frac{1}{2}}$) against Glomerular Filtration Rate (GFR).

In addition, the data were tabulated and are set forth in FIG. 5 herein. It can be seen from the data as presented, that a fairly consistent and linear relationship exists from which can be determined elimination of aminoguanidine and correspondingly normal kidney function. The aminoguanidine $T_{\frac{1}{2}}$ values are thereby used to identify abnormalities in kidney function which can correspondingly be utilized to determine kidney impairment and/or underlying pathological conditions.

This invention may be embodied in other forms or carried out in other ways without departing from the spirit or essential characteristics thereof The present disclosure is, therefore, to be considered as in all respects illustrative and not restrictive, the scope of the invention being indicated by the appended claims, and all changes which come within the meaning and range of equivalency are intended to be embraced therein

What is claimed is:

1. A method for assaying aminoguanidine and its analogs comprising:
   A. gathering a biological sample believed to contain a quantity of aminoguanidine or analogs thereof;
   B. deproteinizeing the biological sample;
   C. reacting the deproteinized biological sample of Step B with a pyridine aldehyde in an amount sufficient to convert any aminoguanidine or analogs thereof present in said biological sample to the corresponding pyridine aldehyde-substituted hydrazone;
   D. isolating any substituted hydrazone formed in Step C from the remainder of the reaction mixture by high pressure liquid chromatography employing an isocratic or gradient elution; and
   E. examining the isolate of Step D to assess the quantity and disposition of said aminoguanidine and/or its analogs.

2. The method of claim 1 wherein the biological sample is selected from the group consisting of plasma, urine and tissue.

3. The method of claim 1 wherein the biological sample is prepared with a known equal amount of an internal standard.

4. The method of claim 3 wherein said internal standard is selected from the group consisting of aminoguanidine and its analogs.

5. The method of claim 4 wherein said internal standard comprises aminoguanidine.

6. The method of claim 4 wherein said internal standard comprises N-ethyl aminoguanidine.

7. The method of claim 1 wherein said biological sample is deproteinized by treatment with a deproteinizing agent selected from the group consisting of moderate to strong acids, and organic solvents capable of precipitating protein.

8. The method of claim 7 wherein said acid is selected from the group consisting of perchloric acid and trichloroacetic acid.

9. The method of claim 7 wherein said organic solvent is selected from the group consisting of methanol, acetonitrile and methylene chloride 10. The method of claim 1 wherein said biological sample is deproteinized by subjecting said sample to ultrafiltration.

11. The method of claim 1 wherein the pyridine aldehyde comprises a picolinaldehyde.

12. The method of claim 11 wherein the pyridinealdehyde comprises 6-methyl picolinaldehyde.

13. The method of claim 1 wherein Step C is performed under mildly acidic conditions.

14. The method of claim 1 wherein the high pressure liquid chromatography protocol of Step D utilizes a radial compression chromatographic column and proceeds with an isocratic flow rate and under paired-ion conditions.

15. The method of claim 1 wherein the examination of Step E comprises detection of any aminoguanidine and/or analogs thereof by ultraviolet spectroscopic analysis of the isolate at a wavelength of about 302 nm.

16. A method for monitoring the status of drug therapy to inhibit the formation of advanced glycosylation end products in the body comprising performing the method of claim 1.

17. A method for screening a new compound that may inhibit the formation of advanced glycosylation end products in the body, comprising determining the absorption, distribution, metabolism and/or excretion profile by preparing biological samples that have been incubated with a quantity of said new compound and examining said samples by the method of claim 1.

* * * * *